United States Patent [19]
Eibl et al.

[11] 3,940,423
[45] Feb. 24, 1976

[54] 1,2-O-DIALKYLMETHYLIDENE-GLYCERO-3-PHOSPHATIDES

[75] Inventors: Hansjörg Eibl, Bovenden; Alfar Nicksch, Goettingen-Nikolausberg, both of Germany

[73] Assignee: Max-Planck-Gesellschaft zur Forderung der Wissenschaften e.V., Goettingen, Germany

[22] Filed: Aug. 28, 1974

[21] Appl. No.: 501,182

[30] Foreign Application Priority Data
Sept. 6, 1973 Germany............................ 2345060

[52] U.S. Cl. ............. 260/340.9; 252/545; 424/199; 424/203; 426/604
[51] Int. Cl.[2] .......................................... C07F 9/10
[58] Field of Search................. 260/340.9, 925, 973

[56] References Cited
UNITED STATES PATENTS
3,577,446  5/1971  Rakhit ............................ 260/944 X
3,708,558  1/1973  Kny et al. .......................... 260/945

OTHER PUBLICATIONS
Newman et al., Journal of the Americal Chemical Society, Vol. 67, (1945) p. 1621.

*Primary Examiner*—Richard L. Raymond
*Attorney, Agent, or Firm*—Hans Berman; Kurt Kelman

[57] ABSTRACT

Glycerol is reacted with a ketone having 19 to 35 carbon atoms to 1,2-O-dialkylmethylidene-glycerol which is phosphorylated by means of β-bromoethylphosphoric acid dichloride. The resulting intermediate is aminated with ammonia, methylamine, dimethylamine, or trimethylamine to a compound of the formula

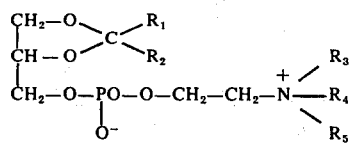

wherein $R_1$ and $R_2$ are alkyl having 9 to 17 carbon atoms, and $R_3$, $R_4$, and $R_5$ are hydrogen or methyl. The compounds and their non-toxic acid addition salts are surfactants which may be employed in detergent compositions or as emulsifiers in food.

4 Claims, No Drawings

1,2-O-DIALKYLMETHYLIDENE-GLYCERO-3-PHOSPHATIDES

This invention relates to lecithin analogs, and particularly to glycerol ether phosphatides and to a method of preparing the same.

In its more specific aspects, the invention relates to phosphatides which are compounds of the formula

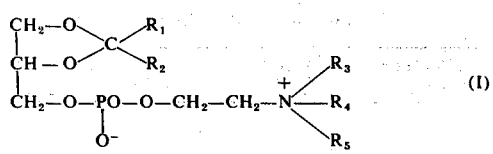

and acid addition salts of such compounds, in the formula $R_1$ and $R_2$ being alkyl having 9 to 17 carbon atoms, and $R_3$, $R_4$, and $R_5$ being hydrogen or methyl.

The compounds of the invention differ from lecithins by a cyclic ether moiety where ester moieties are present in lecithins. The compounds are generally more stable than natural lecithins, but have many of the desirable properties of lecithins, as will be described in more detail hereinbelow.

They are prepared by reacting glycerol with a ketone $R_1 - CO - R_2$ until a 1,2-O-dialkylmethylidene-glycerol of the formula

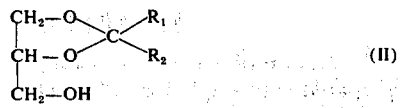

is formed, phosphorylating the compund of Formula (II) with β-bromoethylphosphoric acid dichloride to an intermediate of the formula

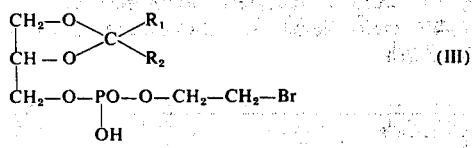

and aminating the intermediate by means of a compound of the formula

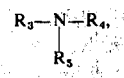

$R_1$ to $R_5$ being as defined above.

The reaction between glycerol and the ketone is carried out in an organic solvent medium in the presence of an acid as a condensation catalyst, p-toluenesulfonic acid being illustrative of suitable acids. A polar organic solvent medium is preferably employed in the phosphorylation step which is carried out under anhydrous conditions. It is convenient to employ the β-bromoethylphosphoric acid dichloride in the form of a salt with an alkylamine, such as triethylamine. The reaction proceeds smoothly at room temperature, but slightly elevated temperatures are permissible. The amination step also is performed in a polar organic solvent medium, preferably in a mixture of chloroform with acetonitrile and/or nitromethane in a preferred ratio of 1:3 to 3:1. The solubility of the aminating agent in the reaction medium may be improved by the further addition of a lower alkanol having up to four carbon atoms, with or without water. These special mixtures of solvents make the amination reactions — especially with $NH_2CH_3$ and $NH_3$ - possible. Room temperature is adequate, and slight warming may be resorted to.

The compounds are conveniently purified by chromatography on silica gel. The pure compounds do not show a characteristic melting point, but are readily identified by elemental analysis and thin layer chromatography. The acid addition salts are formed by combining the solutions of the compounds with solutions of stoichiometric amounts of acids in a common solvent, and by evaporating the solvent until the salt is precipitated.

The compounds and their acid addition salts are biodegradable surfactants suitable for use in detergents and as emulsifiers in foods such as margarine. They also have the ability of modifying the properties of cell membranes in a manner to improve the effects of therapeutic agents.

Enzymes in cell membranes contain mixtures of natural phospholipids which include unsaturated aliphatic acid moieties. Because of the instability of these unsaturated moieties in the presence of oxygen, the enzymes are not stable when isolated. When the enzymes are stripped of their natural lipid component, they lose their enzyme activity, but the delipidized enzymes can be reactivated in stabilized condition by mixing them with the compounds of the invention.

It is thought by biologists that hybrid formation and cell fusion are induced by lysolecithin so that cell hybrids may be produced as by Sendai virus. However, the lysolecithins employed in this work are derived from egg lecithin and have substantial cytolytic activity. Cytolysis can be avoided by using compounds of the invention selected for suitable cytolytic activity.

The following Examples are further illustrative of this invention.

EXAMPLE 1

A mixture of 60 g glycerol (0.65 mole), 180 g dipentadecylketone (0.4 mole), 6 g p-toluenesulfonic acid, and one liter benzene was heated to the boiling point in a two-liter flask equipped with a condenser for the evaporating solvent, a trap for separating much of the water from the distillate, and a drying cartridge filled with magnesium perchlorate through which the benzene collected in the trap was returned to the flask. The heating rate was adjusted to evaporate benzene at a rate of about 200 ml per hour. A magnetic stirrer in the flask maintained intimate contact between the glycerol and the benzene solution.

Most of the water expected from the reaction between the glycerol and the ketone was recovered within about 4 hours, and more than 90% of the dipentadecylketone was converted to 1,2-O-dipentadecyl-methylidene-glycerol (2,2-dipentadecyl-1,3-dioxolane-4-methanol) within 24 hours. The reaction was permitted to continue for 48 hours.

15 g Active carbon was then added to the contents of the flask which were cooled to 5°C and filtered to remove precipitated dipentadecylketone. The filtrate was washed and neutralized by shaking with 500 ml aqueous 5% potassium carbonate solution, and the benzene layer was separated and evaporated. The yellow residue was dissolved in 900 ml hot acetone, the solution was mixed with an equal volume of hot methanol, and the mixture was filtered. The filtrate was cooled to 0°C, and the crystalline precipitate was filtered off with suction and dried in a vacuum desiccator.

130 g Pure 1,2-O-dipentadecylmethylidene-glycerol (62% yield based on the dipentadecylketone) was recovered as a white powder melting at 35° – 40°C. It was identified by elemental analysis.

| Calculated for $C_{34}H_{68}O_3$: | 77.80% C; | 13.06% H |
|---|---|---|
| Found: | 77.94 | 13.05 |

44 g (0.18 Mole) β-bromoethylphosphoric acid dichloride was dissolved in 100 ml anhydrous chloroform, the solution was cooled with ice, and 36 g (0.36 mole) anhydrous triethylamine in 50 ml chloroform was added with stirring. The mixture was then transferred to a water bath at 20°C, and a solution of 50 g (0.095 mole) of the above 1,2-O-dipentadecylmethylidene-glycerol in 250 ml anhydrous chloroform was added dropwise with stirring. After two more hours of stirring at ambient temperature, the glycerol ether could no longer be detected by thin layer chromatography. The reaction mixture was stirred with an equal volume of ice to decompose the phosphorylating agent. The water phase was discarded, and the chloroform phase was evaporated to remove the solvent. The oily residue was dissolved in 300 ml tetrahydrofuran, 60 ml distilled water was added, and the mixture was stirred one hour to complete the decomposition of the β-bromoethylphosphoric acid dichloride. It was then washed sequentially with 400 ml diisopropyl ether, 400 ml 2% formic acid solution, and 100 ml methanol. The aqueous phase having a pH of 2 was discarded.

The diisopropyl ether solution was shaken with 400 ml 0.1-molar sodium acetate solution (pH 5.6) and 100 ml methanol to neutralize the formic acid present, and separated from the aqueous washing liquid. The organic solvent solution was dried 10 minutes by stirring with 20 g sodium sulfate, and the solvent was evaporated. The residue was a yellow oil which was taken up in 450 ml methanol. The solution so obtained was cooled to about 0° – 5°C and stirred for 15 minutes with active carbon. It was then filtered, and the filtrate was diluted with methanol to 600 ml. It contained practically pure 1,2-O-dipentadecylmethylideneglycerol-3-phosphoric acid β-bromoethyl ester ($C_{36}H_{72}BrO_6P$, equivalent weight 711.9), as determined by thin layer chromatography. The yield was 58 g. The methanol solution of this intermediate was stable for many months when stored in a refrigerator.

EXAMPLE 2

7.1 g (0.01 Mole) intermediate prepared by the method of Example 1 was dissolved in 100 ml chloroform, and the solution was mixed with 100 ml acetonitrile in a 500 ml round-bottom flask. A solution of 60 ml trimethylamine in 120 ml ethanol was added, and the reaction mixture was stored in the tightly stoppered flask for 24 hours at 25°C. The solvent was then evaporated, and the residue was shaken with 100 ml chloroform, 120 ml methanol, and 100 ml aqueous 2% formic acid solution.

The chloroform layer was separated from the aqueous liquid, washed with 100 ml 0.1-molar aqueous sodium acetate solution and 120 ml methanol to remove formic acid, dried by stirring for 10 minutes with 10 g sodium sulfate, and evaporated to dryness. The residue was recrystallized from 100 ml ethylmethylketone. 6 g Crude, yellowish 1,2-O-dipentadecylmethylidene-glycerol-3-phosphoric acid choline ester was obtained. It was purified by chromatography, and again recrystallized from ethylmethylketone.

The pure compound was white, weighed 5.1 g (62% yield based on 1,2-O-dipentadecylmethylidene-glycerol), and was identified by elemental analysis.

| Calculated: | 66.16% C; | 11.67% H; | 4.37% N |
|---|---|---|---|
| Found | 66.12 | 11.66 | 4.34 |

EXAMPLE 3

The procedure of Example 2 was repeated, but the trimethylamine was replaced by an equal volume of dimethylamine. After final purification, 1,2-O-dipentadecylmethylidene-glycerol-3-phosphoric acid N,N-dimethylethanolamine ester was obtained as a white powder weighing 4.6 g (58% yield based on 1,2-O-dipentadecylmethylidene-glycerol).

| Calculated: | 67.52% C; | 11.68% H; | 2.07% N; | 4.58% P |
|---|---|---|---|---|
| Found: | 67.41 | 11.59 | 2.16 | 4.62 |

EXAMPLE 4

A solution of 7.1 g (0.01 mole) of the intermediate prepared in Example 1 in 200 ml chloroform was mixed sequentially with 200 ml acetonitrile, 40 ml methanol, and 55 ml methylamine dissolved in about 80 ml ethanol. The reaction mixture was stored 24 hours at 25°C and further worked up as described in Example 2. 4.2 g Pure 1,2-O-dipentadecylmethylidene-glycero-3-phosphoric acid N-methylethanolamine ester was recovered (54% yield based on 1,2-O-dipentadecylmethylidene-glycerol).

| Calculated: | 67.13% C; | 11.57% H; | 2.12% N; | 4.68% P |
|---|---|---|---|---|
| Found: | 66.46 | 11.53 | 2.12 | 4.49 |

EXAMPLE 5

7.1 g (0.01 Mole) intermediate prepared according to Example 1 was dissolved in 50 ml chloroform, and the solution was mixed in a one-liter round-bottom flask sequentially with 100 ml acetonitrile, 100 ml methanol, and 100 ml 25% aqueous ammonium hydroxide solution. The flask was stoppered, and the reaction mixture was kept at 49°C for 24 hours. It was then worked up as described in Example 2.

After purification by chromatography, there was obtained 4.0 g pure 1,2-O-dipentadecylmethylidene-glycero-3-phosphoric acid ethanolamine ester.

| Calculated: | 2.16% N; | 4.78% P |
|---|---|---|
| Found: | 2.15 | 4.70 |

When dipentadecylketone was replaced in the reaction of Example 1 ketones having individual alkyl groups of as few as 9 or as many as 17 carbon atoms, the corresponding 1,2-O-dialkylmethylidene-glycerols were obtained and could be further reacted with β-bromoethylphosphoric acid dichloride and ammonia or amines in the manner described in Examples 2 to 5. Ketones having two equal or two different alkyl groups attached to the carbonyl group reacted equally promptly under the conditions of Example 1.

The compounds of the invention readily form acid addition salts with mineral acids, such as hydrochloric and sulfuric acid, and strong organic acids such as chloroacetic acid and p-toluenesulfonic acid when solutions of stoichiometrically equivalent amounts in common solvents, such as chloroform, are evaporated to dryness.

What is claimed is:

1. A phosphatide which is a compound of the formula

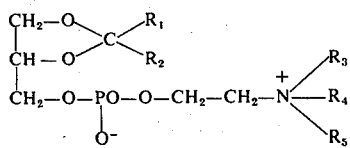

wherein $R_1$ and $R_2$ are alkyl having 9 to 17 carbon atoms, and $R_3$, $R_4$, and $R_5$ are hydrogen or methyl, or an acid addition salt of said compound.

2. A phosphatide as set forth in claim 1 which is an addition salt of said compound with a non-toxic acid.

3. A phosphatide as set forth in claim 1, wherein $R_1$ and $R_2$ are equal.

4. A phosphatide as set forth in claim 1, wherein $R_1$ and $R_2$ are pentadecyl.

* * * * *